United States Patent [19]

Kukes et al.

[11] Patent Number: 4,532,362

[45] Date of Patent: Jul. 30, 1985

[54] OLEFIN OXIDATION CATALYST

[75] Inventors: Simon G. Kukes; Tod K. Shioyama, both of Bartlesville, Okla.

[73] Assignee: Phillips Petroleum Company, Bartlesville, Okla.

[21] Appl. No.: 581,401

[22] Filed: Feb. 17, 1984

Related U.S. Application Data

[62] Division of Ser. No. 364,360, Apr. 1, 1982, Pat. No. 4,448,892.

[51] Int. Cl.$^3$ ............................................. C07C 45/34
[52] U.S. Cl. .................................... 568/401; 568/475; 568/360
[58] Field of Search ................ 568/401, 365, 360, 475

[56] References Cited

U.S. PATENT DOCUMENTS

| | | | |
|---|---|---|---|
| 3,932,521 | 1/1976 | Gloyer et al. | 568/401 |
| 4,152,354 | 5/1979 | Stapp | 568/401 |
| 4,155,879 | 5/1979 | Mimoun et al. | 568/401 |
| 4,220,604 | 9/1980 | Stapp | 568/401 |
| 4,271,320 | 6/1981 | Tokitoh et al. | 568/401 |
| 4,419,525 | 12/1983 | Shioyama et al. | 568/401 |
| 4,434,082 | 2/1984 | Murtha et al. | 568/401 |

*Primary Examiner*—James H. Reamer
*Attorney, Agent, or Firm*—Howard D. Doescher

[57] ABSTRACT

The use of fluorocarbons during the multiphase oxidation of olefins to ketones with Wacker-type catalysts improves reaction efficiency.

14 Claims, No Drawings

OLEFIN OXIDATION CATALYST

This is a divisional application of our copending application having Ser. No. 364,360, filed Apr. 1, 1982, entitled "Olefin Oxidation Catalyst", now U.S. Pat. No. 4,448,892.

BACKGROUND OF THE INVENTION

The Wacker-type oxidation of ethylene to acetaldehyde using a palladium chloride/cupric chloride/hydrochloric acid catalyst in an aqueous solution has been modified and applied to the synthesis of methyl ketones from terminal olefins. However, major problems have been encountered in using the Wacker-type oxidation in the oxidation of higher olefins and internal olefins. One problem is that of reduced rates of reaction due to the low solubility of the olefin in the aqueous medium. Another major problem is the concomitant secondary oxidation of the ketone product which leads to poor selectivities and poor yield of desired product.

The solubility problems encountered in the Wacker-type oxidation of higher olefins have been at least partially solved by resorting to "phase transfer" techniques and the addition of a suitable surfactant. Thus, the prior art teaches that the reaction of the olefinic hydrocarbon reactant to be oxidized in the presence of free oxygen is preferably carried out in a multi-phase diluent system, preferably a two-phase system with one phase aqueous and the other organic. The catalysts known for this multi-phase process are Pd/Cu/alkali metal or alkaline earth metal chloride catalyst or Pd/Cu/boric acid catalyst with the palladium being either free palladium or a palladium compound and the copper component being either a cuprous or a cupric compound. It should also be noted that the HCl used in conventional Wacker oxidation reactions to maintain adequate conversion levels of the olefinic reactant has been eliminated as a component of the multi-phase process. An additional component of this multi-phase prior art reaction system is a suitable surfactant.

Corrosion of metallic process equipment is an additional problem when a catalyst containing halide ions such as the conventional Wacker or modified Wacker-type catalysts are utilized in the oxidation process, and a low-corrosion catalyst can be desirable at times.

THE INVENTION

In accordance with the present invention, a catalytic oxidation process is described wherein the presence of one or more fluorocarbons in a multi-component diluent system improves the efficiency of the catalyst.

In one embodiment of the invention, a catalyst system containing $PdCl_2$, a prepared heteropolyacid $H_9[PMo_6V_6O_{40}]$, cetyltrimethylammonium bromide as phase transfer catalyst, and a solution of water, decane, and perfluorodecalin as a diluent system showed good results in the oxidation of 2-butene to methyl ethyl ketone.

ADVANTAGES

Since fluorinated compounds are very effective oxygen absorbers, their use as solvents or additives for oxidation reactions will decrease reaction time. Their oxygen transfer capability means that less expensive air can be used instead of oxygen in the reactions.

In addition, it has been found that lesser quantities of acetic acid, a poison for the instant catalysts, are produced when the fluorocarbons of the invention are employed. Improvements in conversion and selectivity to desired ketone products are also attained.

OBJECTS OF THE INVENTION

It is one object of the invention to produce a catalyst useful for the oxidation of olefins to ketones.

It is another object of the invention to produce a process whereby ketones can be efficiently produced via the oxidation of olefins.

DESCRIPTION OF THE INVENTION

The invention deals with the use of a fluorocarbon diluent along with other diluents and a multi-component catalyst for the oxidation of olefins.

I. CATALYST SYSTEM

The catalyst utilized according to the instant invention for the oxidation of olefinic hydrocarbons to carbonyl compounds is made up of three components: (1) a palladium component, (2) a heteropolyacid or copper component, and (3) a surfactant component.

(1) Palladium Component

The palladium component of the catalyst system of the instant invention can be any palladium-containing material whose properties render it suitable for use in Wacker or Wacker-type reactions. The palladium component of the invention can be palladium metal, e.g., finely divided palladium powder, or a palladium compound. Examples of suitable palladium compounds include allyl palladium chloride dimer $[C_3H_5PdCl]_2$, dichlorobis(triphenylphosphine)palladium(II), palladium-(II) acetate, palladium(II) acetylacetonate, tetrakis(triphenylphosphine)palladium(O), palladium(II) chloride, palladium(II) iodide, palladium(II) nitrate, palladium-(II) sulfate, and the like. Mixtures of the above palladium compounds can also be utilized as the palladium component of the instant catalyst system if so desired, thus providing a means to minimize the halide content of the catalyst system.

(2) Heteropolyacid or Copper Component

Heteropolyacid Component

The heteropolyacid component of the catalyst system of the instant invention should have a redox potential in excess of 0.5 volt and contain at least two metallic species. It is preferred that it contain molybdenum and vanadium. Such preferred heteropolyacids are defined herein as iso-polymolybdates in which one or more of the molybdenum atoms are replaced by vanadium or an iso-polyvanadate in which one or more of the vanadium atoms are replaced by molybdenum.

The polyacid used contains vanadium atoms, for example from 1 to 8, more preferably 6 atoms, in a molecule, and molybdenum. Typical polyacids for use in the present invention are represented by the following general formula:

$$H_m[X_xMo_aV_bM_yO_z]$$

in which
X is B, Si, Ge, P, As, Se, Te or I;
M is W, Nb, Ta or Re;
m, a, b and z are integers;
x is zero (for mixed isopolyacids) or an integer (for hetero-polyacids);
and y is zero or an integer such that $6 \leqq (y+a+b)/z \leqq 12$ and $m+Nx+6a+5b+N'y \geqq 2z$
in which each of N and N' is the number of the group of the periodic table to which X and M respectively belong. Examples of typical heteropolyacids are as follows:

| Heteropolyacid | Redox potential, V |
| --- | --- |
| $H_9[TeMo_3V_3O_{24}]$ | +0.80 |
| $H_4[As_2Mo_{12}V_6O_{61}]$ | +0.65 |
| $H_3[AsMo_6V_6O_{40}]$ | +0.72 |
| $H_6[SiMo_{10}V_2O_{40}]$ | |
| $H_6[GeMo_{10}V_2O_{40}]$ | |
| $H_n[PMo_pV_qO_{40}]$*, for example: | |
| $H_4[PMo_{11}VO_{40}]$ | +0.65 |
| $H_5[PMo_{10}V_2O_{40}]$ | +0.70 |
| $H_6[PMo_9V_3O_{40}]$ | +0.72 |
| $H_7[PMo_8V_4O_{40}]$ | +0.75 |
| $H_8[PMo_7V_5O_{40}]$ | +0.76 |
| $H_9[PMo_6V_6O_{40}]$ | +0.77 |
| $H_{10}[PMo_5V_7O_{40}]$ | +0.79 |
| $H_{11}[PMo_4V_8O_{40}]$ | +0.80 |
| $H_5[Mo_rW_mV_2O_{40}]$** | |
| $H_9[PMo_3W_3V_6O_{40}]$ | +0.70 |

*in which $n = 3 + q$, $p = 12 - q$, $q = 1$ to 10
**in which $m = 2, 4, 6$, or 8 and $r = 10 - m$.

The ratios of the various catalyst components can be expressed in terms of a molar ratio of heteropolyacid to palladium. The molar ratio of heteropolyacid component to palladium component in the instant catalyst system is broadly about 1/1 up to 50/1.

The amount of catalyst employed according to the instant invention can be expressed in terms of the molar ratio of olefinic hydrocarbon reactant to palladium component of the catalyst system. Broadly, the molar ratio of olefinic reactant to palladium component is from about 5/1 up to 1000/1 and preferably from about 10/1 up to 250/1.

Copper Component

The copper component of the instant catalyst system can be provided by utilizing a cuprous or cupric compound or mixture thereof. A wide variety of copper compounds can be utilized to provide the copper component of the instant catalyst system. Specific examples of suitable copper compounds include copper(I) acetate, copper(II) acetylacetonate, copper(I) bromide, copper(I) chloride, copper(II) chloride, copper(I) iodide, copper(II) nitrate, and the like. Mixtures of suitable copper compounds can also be employed to provide the copper component of the instant catalyst system if so desired.

Mixtures of heteropolyacids and copper compounds can be employed.

(3) Surfactant Component

Generally, the surfactant component of the reaction system according to the instant invention comprises one or more compounds which exhibit surface-active properties—i.e., surfactants. However, the term "surfactant" encompasses a very broad class of compounds, and it has been discovered that not all surfactants are suitable for use in the instant invention. Nevertheless, for convenience and simplicity, the suitable compounds that can be employed according to the instant invention and described more fully below will be termed surfactants herein. At the present time, it is not known whether, in the catalyst and process of the invention, these compounds function as phase-transfer catalysts, such as is taught in the art, or whether they function as micellar catalysts, a feature also disclosed in the prior art. Because of this uncertainty in the mode of action of these compounds in the instant invention, and for convenience, the following compounds will merely be described herein as surfactants.

A preferred surfactant for use in the reaction system of the instant invention is selected from one of the five following groups:

(A) Quaternary ammonium salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms broadly and preferably from 16 to 22 carbon atoms; and wherein X is selected from the group consisting of $Br^-$, $Cl^-$, $I^-$, $F^-$, $R'''CO_2^-$, $QSO_3^-$, $BF_4^-$, and $HSO_4^-$, wherein Q is an aryl, alkaryl or arylalkyl radical of 6 to 10 carbon atoms. It will be noted that a variety of anions are suitable as the $X^-$ component of the quaternary ammonium salts.

Useful quaternary ammonium salts according to the general formula given above include cetyltrimethylammonium bromide, hexadecyltrimethylammonium bromide, tetraheptylammonium bromide, cetyltrimethylammonium stearate, benzyltributylammonium chloride, benzyltriethyl-ammonium bromide, benzyltrimethylammonium bromide, phenyltrimethyl-ammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, and tetrabutylammonium tetrafluoroborate.

(B) Alkali metal alkyl sulfates of the general formula $R'^vOSO_3M$, wherein $R'^v$ is an alkyl radical having from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate and the like.

(C) Alkali metal salts of alkanoic acids of the general formula $R'^vCO_2M$, wherein $R'^v$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and the like.

(D) Alkali metal salts of alkaryl sulfonic acids of the general formula

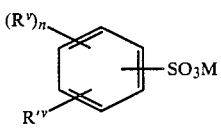

wherein $R'^v$ and M have the same meaning as given and wherein $R^v$ is an alkyl radical of 1 to 4 carbon atoms and wherein n is 0 or an integer of from 1 to 4. Typical compounds within the (D) group include sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium octadecylbenzenesulfonate, potassium octadecylbenzenesulfonate, sodium eicosylbenzenesulfonate, potassium dodecyltoluenesulfonate, sodium dodecylxylenesulfonate and the like.

(E) 1-Alkyl pyridinium salts of the general formula

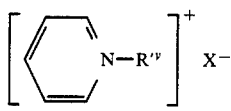

wherein $R'^v$ and $X^-$ have the same meanings as described above. Examples of suitable 1-alkyl pyridinium salts are 1-dodecylpyridinium paratoluenesulfonate, 1-dodecylpyridinium chloride, 1-hexacylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to the instant invention can be expressed in terms of a mole ratio based on the palladium component of the catalyst system. Broadly, the mole ratio of surfactant to palladium compound will be from 0.01/1 to 10/1. Preferably, it will be from 0.1/1 to 3/1.

II. DILUENT SYSTEM

As indicated above, the oxidation of the olefinic hydrocarbon according to the instant invention is carried out in the presence of a diluent comprised of at least two liquid phases, wherein at least one of which is an aqueous phase and at least one contains a fluorocarbon compound.

The Organic Phase

The nonaqueous phase will hereinafter be termed the organic phase. It should be understood that "organic" is intended to include the fluorocarbon additives of this invention. Said organic phase should be relatively unaffected by the oxidation conditions, of course, and also be relatively unaffected by hydrolysis-type reactions. Furthermore, it is apparent that if at least two phases are present, at least one of which is an aqueous phase, that the organic diluent utilized must have somewhat limited solubility in the aqueous phase. In addition, the choice of the organic diluents may be often determined based on the difference in boiling points expected between the product of the oxidation reaction and the organic diluents so as to facilitate separation of the components of the reaction mixture. Within these general requirements, a rather broad range of organic compounds can be utilized to form the organic phase according to the instant invention.

(A) Flourocarbon Diluents

The fluorocarbon constituent of the organic phase is one or more fluorinated hydrocarbons. Typically, they are compounds in which the number of fluorine atoms present on the molecule is equal to or greater than the number of atoms of halogens other than fluorine. Useful fluorocarbons include compounds containing from 1 to about 24 carbon atoms. Examples are methyl 1-perfluorodecalin, dichlorotetrafluorobenzene, monochloropenta-fluorobenzene, tetrachlorooctafluorocyclohexane, and the like.

One preferred group of fluorocarbons are compounds devoid of hydrogen which conform to the empirical formula:

$$C_xF_yX_z$$

where X is a halogen other than fluorine, $y > x$, and $y > z$. Perhalogenated compounds, especially perfluorinated compounds, are preferred. Compounds of this type are generally aliphatic or cycloaliphatic. They include perfluorodecalin, perfluorocyclopentane, trichloropentafluorocyclobutane, monochlorononafluorobutane, tetrafluoromethane and the like. Mixtures of fluorocarbons are operable.

While the fluorocarbons are characterized as diluents, it is believed that they function as oxygen transfer agents as well. Accordingly, oxidations conducted using fluorocarbon additives proceed faster than those conducted without them.

(B) Non-fluorocarbon Diluents

Generally speaking, suitable compounds can be found in the classes of compounds described as aliphatic hydrocarbons, aromatic hydrocarbons or alkylsubstituted aromatic hydrocarbons, halogenated aromatic compounds, and esters of aromatic carboxylic acids although the latter may be less preferred because of a tendency toward hydrolysis of the ester group in certain instances. In addition, it has been found that compounds such as nitrobenzene and benzonitrile, commonly utilized as solvents for many organic reactions, show a definite inhibitory effect on the reaction of the instant invention presumably by complexing of one or more catalyst components.

Suitable organic diluents include cyclohexane, hexane, octane, decane, dodecane, tetradecane, hexadecane, benzene, toluene, chlorobenzene, methylbenzoate, bromobenzene, 1,3,4-trichlorobenzene, ortho-dichlorobenzene, sulfolane, ortho-xylene, para-xylene, meta-xylene, methylcyclopentane, dimethyl orthophthalate, and the like. Mixtures of organic diluents may be utilized in some cases as desired.

Diluent Combinations

The amounts of the aqueous phase and organic diluent phase based on the starting olefinic reactant can vary over a wide range, and a suitable range includes from about 20 to 0.2 volumes of organic diluent per volume of olefinic hydrocarbon reactant, preferably from about 5 to 1 volumes of organic diluent per volume of olefinic hydrocarbon reactant. Similarly, the broad range for the amount of aqueous phase is from 20 to 0.2 volumes per volume of olefinic hydrocarbon reactant and preferably from 5 to 1 volumes per volume of olefinic hydrocarbon reactant.

It is worth pointing out some predictions relating to the expected effects of the volume of aqueous phase on the oxidation reaction of the instant invention. First, if the aqueous phase volume becomes too small, the concentration of the catalyst components in the aqueous phase can cause a decrease in the solubility of the olefinic hydrocarbon reactant in the aqueous phase, thus greatly slowing down the reaction rate wherein the olefinic hydrocarbon reactant is oxidized to the desired carbonyl compound. Secondly, if the aqueous phase becomes too large, the concentration of catalyst components can be so dilute that the reaction with the olefinic hydrocarbon can also be greatly slowed. However, it can be seen that a judicious choice of the optimum amount of the aqueous phase for high conversion levels of the olefinic hydrocarbon reactant can readily be determined by a few well-chosen experiments.

At present, it is believed that the primary function of the organic phase in the reaction system of the instant invention is to greatly increase the selectivity to the desired carbonyl compound by effectively removing the carbonyl compound product from the locus of the oxidation reaction thereby preventing side reactions such as isomerization and/or further oxidation of the carbonyl compound. However, this explanation is to be treated merely as one possible theory of the mode of action of the organic phase in the reaction and applicants should not be bound to same.

III. OXYGEN

As indicated previously, the reaction of the instant invention is an oxidation reaction whereby an olefinic reactant is converted to a carbonyl compound in the presence of a catalyst and diluent system described above. Thus, the reaction of the instant invention is carried out in the presence of free oxygen. The oxygen may be supplied to the reaction mixture essentially as pure oxygen or in admixture with other gases which are essentially inert to the reaction conditions. Air can be utilized as a source of oxygen for the oxidation reaction of this invention.

As is generally true for most oxidation reactions, the reaction of the instant invention can be exothermic and thus some care should be exercised in controlling the amount of oxygen present in the reaction system. For this reason, and also to improve control of the temperature of the reaction, it is preferred to add oxygen or the gaseous mixture containing oxygen to the reaction zone incrementally so that explosive oxygen concentrations do not develop. The pressure of oxygen utilized for the instant invention can be from about 2 up to 250 psig and, preferably, from about 10 to 100 psig above the autogenous pressure at the temperature utilized.

IV. OLEFINIC HYDROCARBON REACTANT

The olefinic hydrocarbon reactant which is oxidized according to the process of the instant invention can be selected from the groups consisting of acyclic olefinic compounds containing from 2–20 carbon atoms per molecule, preferably 3–12, and having 1, 2, or 3 olefinic carbon-carbon double bonds per molecule and cyclic olefinic compounds containing from 5–20 carbon atoms per molecule and having 1, 2, or 3 olefinic carbon-carbon double bonds per molecule. Within the limitations described above, suitable olefinic hydrocarbon reactants can be represented by the general formula RCH=CHR' wherein R and R' are selected from the group consisting of hydrogen, alkyl, alkenyl, alkadienyl, cycloalkyl, cycloalkenyl, and cycloalkadienyl radicals and wherein R can be the same or different from R' and wherein R and R' taken together can form an alkylene or alkenylene or alkadienylene radical thus forming a cyclic system. The term "olefinic carbon-carbon double bond" as used herein is not meant to include those carbon-carbon double bonds which are part of an aromatic carbocyclic system of alternating single and double bonds.

Examples of suitable monoolefinic compounds are ethylene, propylene, 1-butene, 2-butene, 1-pentene, 2-pentene, 1-hexene, 2-hexene, 1-octene, 1-decene, 1-dodecene, 1-hexadecene, 1-octadecene, 1-eicosene, vinyl cyclohexane, cyclopentene, cyclohexene, cycloheptene, cyclooctene, cyclododecene, 3,3-dimethyl-1-butene, and the like.

Examples of suitable diolefinic compounds are 1,3-butadiene, 1,3-pentadiene, 1,5-hexadiene, 4-vinylcyclohexene, 1,5-cyclooctadiene, 1,9-decadiene, 1,7-octadiene, 1,3-cycloheptadiene, and the like.

Suitable triolefinic compounds include 1,5,9-cyclododecatriene, cycloheptatriene, 1,6-diphenyl-1,3,5-hexatriene, and the like.

While the double bond unsaturation can be internal or non-terminal, it is preferred that at least one olefinic carbon-carbon double bond be in the terminal position. That is, the preferred olefinic reactant has at least one terminal olefinic or vinyl group. Mixtures of olefinic reactants can be employed.

V. REACTION CONDITIONS

The particular temperature employed may be dependent somewhat on the olefinic hydrocarbon reactant. For example, at relatively high temperatures, a lower molecular weight olefinic hydrocarbon reactant may tend to be very insoluble in the aqueous phase of the two-phase system of the instant invention, thus causing a reduced conversion of the olefinic hydrocarbon reactant. On the other hand, a higher molecular weight olefinic reactant may be able to tolerate a higher reaction temperature and still maintain a reasonable degree of solubility in the aqueous phase and thus achieve a good degree of conversion at the higher temperature. The temperature utilized in the instant invention is broadly from about 20° to 200° C. and preferably from about 60° to 150° C. Most preferably it lies between about 70° and 100° C.

The time employed for the reaction according to the instant invention can vary over a wide range and will, to some extent, depend on the desired degree of conversion of the olefinic hydrocarbon reactant. Generally, a time period such as from 30 minutes to 8 hours will be employed in the instant invention, preferably 1 to 3 hours.

Because the oxidation reaction according to the instant invention is carried out in the presence of a diluent system comprising at least two liquid phases, it is expected that good stirring will be beneficial. Conventional means of achieving good agitation and contact between the liquid phases can be employed.

The charge order of the reaction components and catalyst components is not critical in the process of the instant invention. However, the presence of oxygen in the reaction mixture prior to heating of the mixture to the desired reaction temperature appears to promote higher selectivity to the desired carbonyl compound.

The process of the instant invention can be carried out in either a batch or continuous process.

Reaction vessels and conduits utilized in the process of the instant invention should, of course, be able to withstand the oxidizing conditions which are present. For this reason, glass-lined, tantalum, titanium or Hastelloy C-clad vessels and conduits are recommended for use in the process of this invention.

VI. REACTION MIXTURE WORKUP

A variety of methods can be utilized to recover the products, unreacted olefinic hydrocarbon starting materials, and the catalyst in the aqueous phase in the instant invention. For example, the entire reaction mixture can be subjected to a fractional distillation to separate the components into various fractions or portions. The bottoms from said distillation can be recycled to the reaction zone as that portion contains essentially all of the catalyst system for the reaction.

Another method of treating the reaction mixture is to contact the entire mixture with a lower alkane such as n-pentane, then separate the aqueous phase from the organic phase, with subsequent fractional distillation of the organic phase to recover the products and any unreacted olefinic hydrocarbon reactants. The aqueous phase can be recycled to the reaction zone as described above, since it contains essentially all of the catalyst components.

Another method of reaction mixture workup involves admixture of the reaction mixture with a saturated aqueous sodium chloride solution followed by extraction of the mixture into diethyl ether. The ether extract can then be distilled or treated in such a manner as to remove the ether leaving the organic residue containing the product and any unreacted olefinic hydrocarbon reactant. Said residue can then be subjected to fractional distillation procedures to recover the various components.

VII. PRODUCT UTILITY

As indicated earlier, the reaction of the instant invention provides a process for the conversion of olefinic hydrocarbon reactants to carbonyl compounds. Said carbonyl compounds are ketones, except for the case of ethylene oxidation which yields acetaldehyde. If the olefinic hydrocarbon reactant contains two carbon-carbon double bonds, the product can be an unsaturated monoketone or diketone. Furthermore, the unsaturated monoketone can be recycled to the reaction zone for conversion to the diketone. Similarly a triolefinic reactant can be converted to intermediates such as unsaturated mono- or diketones and ultimately to a triketone. Ketones from the olefinic hydrocarbon reactants described in part IV above have generally well-known utilities. For instance, they can be utilized as solvents (e.g., methyl ethyl ketone) or as intermediates in the synthesis of other chemical compounds (e.g., pinacolone).

VIII. EXAMPLES

In all of the runs that are described in the following examples, the reaction vessel utilized was a 300 cc titanium Magnedrive stirred tank reactor sold by Autoclave Engineers or a 500 mL Fischer-Porter compatability aerosol bottle. The autoclave was heated by an electric heater and controlled by a Thermoelectric 400 temperature controller. The Fisher-Porter bottles were fitted with pressure gauges, vent and chargelines through which oxygen could be added continuously or incrementally. The oxygen line to the reaction vessel was fitted with the appropriate check valves and flame arrestor. The bottle was heated in an ethylene glycol bath, and monitored on an Acromag by a thermocouple placed in the glycol bath. The bottle contents were stirred by a magnetic stirrer.

For autoclave runs, the reactor was charged with the catalyst system, the diluents, and then sealed. Thirty psig oxygen pressure was introduced to pressure test the reactor, then vented. The olefinic reactant was then charged, while autoclave stirring was begun to aid olefin dissolution in the organic diluent. Thirty psig oxygen pressure was again introduced and the autoclave heated to the desired reaction temperature before the oxygen pressure was adjusted to the desired operating pressure. The reaction was allowed to take-up oxygen on demand for the duration of the reaction in order to maintain the desired pressure. For runs carried out in the Fischer-Porter bottles, the catalyst, diluents, and olefinic reactant were charged. The bottle was assembled with the proper fittings, placed in the ethylene glycol bath, and stirring begun. An initial pressure of 30 psig oxygen was introduced, the reaction mixture heated to the desired reaction temperature, then oxygen pressure raised to the desired reaction value. As above, the system was allowed to take-up oxygen on demand to maintain the desired operating pressure throughout the reaction.

After the desired reaction time had elapsed the reaction was cooled to room temperature before excess oxygen was vented. The combined organic and aqueous phases were subjected to conventional fractional distillation to recover volatile materials (starting material, products and by-products). For catalyst recycle, the residual materials were returned directly to the reactor or were phase separated after distillation, decane solvent being recycled to the reactor while the aqueous phase was evaporated to dryness, the residue redissolved in deionized water, $H_2SO_4$ added to adjust pH to 1.9, and the resulting solution then recycled to the reactor. All samples were analyzed by gas-liquid phase chromatography.

EXAMPLE I

Preparation of the Phospho-6-molybdo-6-vanadic acid 45.5 g $Na_3PO_4.12H_2O$ (0.12 mol), 103.6 g $MoO_3$ (0.72 mol), 42.0 g $V_2O_5$ (0.23 mol) and 22.4 $Na_2CO_3.10H_2O$ (0.08 mol) were dissolved in 600 mL $H_2O$. The solution was heated to boiling and stirred vigorously for 40 minutes. The solution gradually turned an intense brownish-red. The solution volume was reduced to 150 mL by evaporation, then allowed to cool to room temperature. The pH of the solution was adjusted to 1.00 with concentrated sulfuric acid, the solution was then filtered and set aside for use as a component in the inventive oxidation process.

EXAMPLE II

A series of 1-butene oxidations were carried out utilizing the same catalyst charge for numerous recycles, with intermittent replenishing of catalyst components (as noted in Table I, below) to compensate for handling losses associated with catalyst recycle. The aqueous phase was dried and redissolved in fresh water between each run. All reactions were carried out in a 500 mL Fischer-Porter bottle containing 100 mL water, 100 g (137 mL) decane, and reagents in the amounts tabulated in Table I. Reactions were carried out for 1 hour at 80° and 100 psig according to the general procedure set forth above.

TABLE I

| Run # | PdCl$_2$, mol | HPA*, mol | CTMAB**, mol | Butene Charged, mol | Butene Conversion, mol % | Selectivity to MEK, mol % |
|---|---|---|---|---|---|---|
| 1 | 0.01 | 0.05 | 0.004 | 0.35 | 47.9 | 92.7 |
| 2 | " | " | " | 0.35 | 41.4 | 94.5 |
| 3 | +.001 | " | +.0003 | 0.37 | 65.7 | 91.4 |
| 4 | " | " | " | 0.37 | 55.8 | 91.1 |
| 5 | +.001 | " | +.0003 | 0.38 | 62.7 | 91.9 |
| 6 | " | " | " | 0.35 | 67.5 | 92.2 |
| 7 | +.001 | " | +.0003 | 0.34 | 66.6 | 93.3 |
| 8 | " | " | " | 0.36 | 73.6 | 91.7 |
| 9 | +.001 | " | +.0003 | 0.38 | 75.3 | 93.3 |
| 10 | " | " | " | 0.37 | 69.5 | 92.8 |
| 11 | " | " | " | 0.38 | 67.9 | 93.3 |
| 12 | " | " | " | 0.37 | 50.5 | 96.4 |
| 13 | " | " | " | 0.38 | 68.3 | 94.5 |

*heteropolyacid
**cetyltrimethylammonium bromide

This example demonstrates that the palladium chloride/heteropolyacid/surfactant catalyst system in 2-phase medium is an effective oxidation catalyst for the conversion of 1-butene to MEK.

EXAMPLE III

A series of 1-butene oxidations were carried out utilizing the same catalyst charge for numerous recycles, with intermittent replenishing of catalyst components (as noted in Table II, below) to compensate for handling losses associated with catalyst recycle. The aqueous phase was dried and redissolved in fresh water between each run. All reactions were carried out using a 500 mL Fischer-Porter bottle containing 100 mL water, 100 g (137 mL) decane and reagents in the amounts tabulated in Table II. Reactions were carried out for 2 hours at 80° and 100 psig according to the general procedure set forth above.

TABLE II

| Run # | PdCl$_2$, mol | HPA*, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.45 | 56.0 | 92.7 |
| 2 | " | " | " | 0.45 | 65.0 | 92.8 |
| 3 | +00.001 | " | +0.0003 | 0.46 | 70.5 | 91.4 |
| 4 | " | " | " | 0.43 | 80.2 | 90.5 |
| 5 | +00.001 | " | +0.0003 | 0.46 | 77.6 | 92.3 |
| 6 | " | " | " | 0.46 | 80.5 | 90.0 |
| 7 | +00.001 | " | +0.0003 | 0.46 | 79.3 | 91.9 |
| 8 | " | " | " | 0.45 | 80.0 | 91.2 |
| 9 | +00.001 | " | +0.0003 | 0.48 | 88.4 | 90.6 |
| 10 | " | " | " | 0.44 | 89.0 | 90.0 |
| 11 | +00.001 | " | +0.0003 | 0.46 | 89.8 | 93.0 |
| 12 | " | " | " | 0.45 | 88.0 | 93.6 |
| 13 | " | " | " | 0.44 | 92.6 | 92.0 |
| 14 | " | " | " | 0.45 | 75.3 | 95.5 |
| 15 | " | " | " | 0.45 | 85.7 | 93.7 |

*heteropolyacid

This example demonstrates that the palladium chloride/heteropolyacid/surfactant catalyst system in 2-phase medium is an effective oxidation catalyst for the conversion of 1-butene to MEK.

EXAMPLE IV

The oxidation of 1-butene was carried out in a 300 mL titanium autoclave following the general procedure set forth above. Fifty mL of water, 50 g (68.5 mL) decane, 0.005 mol PdCl$_2$, 0.025 mol of phospho-6-molybdo-6-vanadic acid, and 0.002 mol cetyltrimethylammonium bromide and 1-butene as specified in Table III were charged to the reactor and treated for 2 hrs. at 80° C. and 100 psig.

TABLE III

| Run # | Butene Charged, mol | Butene Conversion, mol % | Selectivity to MEK, mol % |
|---|---|---|---|
| 1 | 0.61 | 64.0 | 95.2 |
| 2* | 0.48 | 61.6 | 92.0 |

*Employing decane and aqueous phase as recovered upon workup of run #1.

This example demonstrates that the palladium chloride/heteropolyacid/surfactant catalyst system in 2-phase medium is an effective oxidation catalyst for the conversion of 1-butene to MEK.

EXAMPLE V

A series of 1-butene oxidations were carried out utilizing the same catalyst charge for several recycles, with intermittent replenishing of catalyst components (as noted in Table IV) to compensate for handling losses associated with reaction. The decane and aqueous phases were returned to the reactor as recovered upon workup. All reactions were carried out using a 300 mL titanium autoclave following the general procedure set forth above. Fifty mL of water, 50 g (68.5 mL) decane, 0.005 mol PdCl$_2$, 0.025 mol of heteropolyacid, 0.002 mol CTMAB, and 1-butene/methyl-1-perfluorodecalin ($C_{11}F_{20}$) mixtures as specified in Table IV were charged to the reactor and treated for 1 hr. at 80° C. and 100 psig.

TABLE IV

| Run # | Methyl-1-perfluorodecalin mol | 1-Butene Charged, mol | Butene Conversion, mol % | Selectivity to MEK, mol % |
|---|---|---|---|---|
| 1 | 0.03 | 0.59 | 33.6 | 100 |
| 2 | +0.03 | 0.54 | 40.9 | 99.8 |
| 3 | "* | 0.45 | 60.6 | 99.7 |
| 4 | "* | 0.66 | 30.2 | 99.8 |
| 5 | +0.01 | 0.47 | 51.4 | 99.8 |

*No additional fluorocarbon provided for this run.

This example demonstrates that the palladium chloride/heteropolyacid/surfactant catalyst system in 2-phase medium with added methyl-1-perfluorodecalin gives excellent selectivity to MEK. Note also the excellent butene conversion in only one hour reaction with much higher butene loading than in control run (Example II) and half the catalyst as used in the control run.

EXAMPLE VI

A series of 1-butene oxidations were carried out utilizing the same catalyst charge for several recycles, with intermittent replenishing of catalyst components (as noted in Table V) to compensate for handling losses associated with reaction workup. The decane and aqueous layers were returned to the reactor as recovered upon workup unless noted otherwise. All reactions were carried out using a 300 mL titanium autoclave following the general procedure set forth above. Fifty mL of water, 50 g (68.5 mL) decane, 0.005 mol PdCl$_2$, 0.025 mol of heteropolyacid, 0.002 mol CTMAB and 1-butene+perfluorodecalin as specified in Table V were charged to the reactor and treated for 2 hrs. at 80° C. and 100 psig.

TABLE V

| Run # | Perfluorodecalin, mol | Butene Charged, mol | Butene Conversion, mol % | Selectivity to MEK, mol % |
|---|---|---|---|---|
| 1 | 0.03 | 0.46 | 59.5 | 98.5 |
| 2 | +0.01 | 0.38 | 85.4 | 97.0 |
| 3 | +0.01 | 0.50 | 71.8 | 98.9 |
| 4 | +0.01 | 0.45 | 84.5 | 98.3 |
| 5 | +0.01 | 0.48 | 46.5 | 88.3 |
| 6* | 0.03 | 0.36 | 66.1 | 97.7 |

*Catalyst was regenerated by evaporating aqueous layer to dryness and redissolving in fresh water as described above; and fresh decane (50 g) was added, along with new charge of perfluorodecalin.

This example demonstrates that the palladium chloride/heteropolyacid/surfactant catalyst system in 2-phase medium with added perfluorodecalin gives excellent selectivity to MEK, with excellent butene conversions as well.

EXAMPLE VII

Several oxidation reactions were carried out employing 1-dodecene as substrate. Reactions were carried out in the 300 mL titanium autoclave according to the general procedure described above. The standard charge included 50 mL water and 50 g (68.5 mL) decane. Other reagents added are designated in Table VI.

TABLE VI

| Run # | Catalyst System* | Fluorocarbon Diluent**, mol | Reaction Conditions Time Hr. | Reaction Conditions Temp, °C. | Reaction Conditions Pressure, psig | Dodecene Charged, mol | Dodecene Conversion, mol % | Selectivity to 2-dodecanone, mol % |
|---|---|---|---|---|---|---|---|---|
| 1 | Pd/Cu/CTMAB | None | 2 | 120 | 400 | 0.09 | 84.8 | 98.8 |
| 2 | Pd/Polyacid/CTMAB | PFD, 0.03 | 2 | 100 | 400 | 0.09 | 3.7 | 48.6 |
| 3 | Pd/Cu/H$_3$BO$_3$ | PFD, 0.03 | 2 | 120 | 400 | 0.09 | 0 | 0 |
| 4 | Pd/Cu/CTMAB | PFD, 0.03 | 2 | 120 | 400 | 0.09 | 93.7 | 99.4 |
| 5 | Pd/Cu/CTMAB | PFB, 0.09 | 2 | 120 | 400 | 0.09 | 86.0 | 98.8 |
| 6 | Pd/Cu/CTMAB | PFH, 0.04 | 2 | 120 | 400 | 0.09 | 89.2 | 95.9 |
| 7 | Pd/Cu/CTMAB | PFP, 0.05 | 2 | 120 | 400 | 0.09 | 98.1 | 99.4 |
| 8 | Pd/Cu/CTMAB | DFB, 0.13 | 2 | 120 | 400 | 0.09 | 82.1 | 99.8 |

*Std. charge:
PdCl$_2$ - 0.01 mol/CuCl$_2$ -0.03 mol/Cetyltrimethylammonium bromide-0.004 mol of phospho-6-molybdo-6-vanadic acid-0.05 mol, H$_3$BO$_3$ -0.25 mol
**PFD = perfluorodecalin
PFB = pentafluorobenzene
PFH = perfluorohexane
PFP = perfluoropentane
DFB = p-difluorobenzene This example demonstrates the enhanced olefin conversion obtained upon oxidation in two-phases with palladium/copper/surfactant catalyst in the presence of added fluorinated diluent. Thus, the addition of fluorocarbon to the oxidation medium for long chain olefins gives improved results over runs carried out in the absence of added fluorocarbon. The perfluorinated compounds are seen to be effective promoters while the "partially" fluorinated compounds difluorobenzene (C$_6$H$_4$F$_2$) and pentafluorobenzene (C$_6$HF$_5$) are not effective.

Reasonable variations, such as those which would occur to a skilled artisan, can be made herein without departing from the scope of the invention.

We claim:

1. In a process for the conversion of olefinic reactants to carbonyl compounds which comprises contacting
   (a) at least one olefin with
   (b) oxygen in
   (c) a reaction diluent comprising at least two liquid phases wherein at least one phase is an aqueous phase and at least one phase is an organic phase, in the presence of
   (d) a catalyst comprising (1) one or more suitable palladium components and (2) one or more suitable heteropolyacid or copper components, and
   (e) one or more surfactants selected from the group consisting of quaternary ammonium salts, alkali metal sulfates, alkali metal salts of alkanoic acids, alkali metal salts of alkaryl sulfuric acids, and 1-alkyl pyridinium salts, the improvement comprising including in said reaction diluent at least one fluorocarbon compound conforming to the formula

$$C_{X'}F_{Y'}X_{Z'}$$

wherein X is a halogen other than fluorine and Y' is greater than X' and Y' is greater than Z', under such oxidation conditions sufficient to oxidize the olefinic carbon-carbon double bond of (a) to a carbonyl group.

2. A process according to claim 1 wherein said olefin is selected from
   (a) acyclic olefinic compounds containing from 2–20 carbon atoms per molecule and having 1, 2, or 3 olefinic carbon-carbon double bonds per molecule and
   (b) cyclic olefinic compounds containing from 5–20 carbon atoms per molecule and having 1, 2 or 3 olefinic carbon-carbon double bonds per molecule.

3. A process according to claim 2 wherein said olefin is 1-butene, 2-butene, a mixture thereof, or 1-dodecene.

4. A process according to claim 1 wherein said reaction diluent additionally contains a hydrocarbon.

5. A process according to claim 4 wherein said hydrocarbon is decane.

6. A process according to claim 1 wherein said fluorocarbon compound is methyl-1-perfluorodecalin or perfluorodecalin.

7. A process according to claim 1 wherein the amount of organic diluent of the two-phase diluent is in the range of about 20 to about 0.2 volumes of organic diluent to sone volume of olefin reactant and the amount of aqueous phase is in the range of about 20 to about 0.2 volumes per volume of olefin reactant.

8. A process according to claim 1 wherein:
   the molar ratio of heteropolyacid or copper to palladium is about 1/1 to 50/1;

the molar ratio of surfactant to palladium is about 0.01/1 to 10/1;

the molar ratio of olefin to palladium is about 5/1 to 1000/1;

the pressure of oxygen in the reaction system is in the range of about 2 to about 250 psig above the autogeneous pressure at the temperature utilized; and the reaction temperature is in the range of about 20° C. to about 200° C.

9. A process according to claim 1 wherein said surfactant (e) is selected from the group of:

(A) Quaternary ammoniums salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms; and wherein X is selected from the group consisting of $Br^-$, $Cl^-$, $I^-$, $F^-$, $R'''CO_2^-$, $QSO_3^-$, $BF_4^-$, and $HSO_4^-$, wherein Q is an aryl, alkaryl or arylalkyl radical of 6 to 10 carbon atoms;

(B) Alkali metal alkyl sulfates of the general formula $R'^vOSO_3M$, wherein $R'^v$ is an alkyl radical having from 10 to 20 carbon atoms and wherein M is an alkali metal;

(C) Alkali metal salts of alkanoic acids of the general formula $R'CO_2M$, wherein $R'^v$ and M have the same meaning as given above for the compounds of (B);

(D) Alkali metal salts of alkaryl sulfonic acids of the general formula

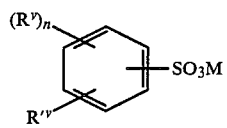

wherein $R'^v$ and M have the same meaning as given and wherein $R^v$ is an alkyl radical of 1 to 4 carbon atoms and wherein n is 0 or an integer of from 1 to 4; and (E) 1-Alkyl pyridinium salts of the general formula

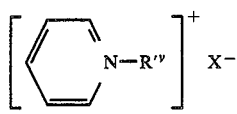

wherein $R'^v$ and $X^-$ have the same meanings as described above.

10. A process according to claim 9 wherein said surfactant is cetyltrimethylammonium bromide.

11. A process according to claim 1 wherein said catalyst (d) is palladium chloride and $Hg[PMo_6V_6O_{40}]$ or palladium chloride and $CuCl_2$.

12. A process according to claim 11 wherein said reaction diluent (c) comprises water, decane and perfluorodecalin.

13. A process according to claim 12 wherein said surfactant (e) is cetyltrimethylammonium bromide.

14. A process according to claim 13 wherein said olefin is at least one of 1-butene, 2-butene, and 1-dodecene.

* * * * *

UNITED STATES PATENT AND TRADEMARK OFFICE
CERTIFICATE OF CORRECTION

PATENT NO. : 4,532,362
DATED : Jul. 30, 1985
INVENTOR(S) : Simon G. Kukes; Tod K. Shioyama It is certified that error appears in the above-identified patent and that said Letters Patent is hereby corrected as shown below:

Claim 7, line 4, "sone" should be "one".

Signed and Sealed this

Fifteenth Day of October 1985

[SEAL]

Attest:

Attesting Officer

DONALD J. QUIGG

Commissioner of Patents and
Trademarks—Designate